(12) United States Patent
Mim

(10) Patent No.: US 10,595,809 B2
(45) Date of Patent: Mar. 24, 2020

(54) MEDICAL IMAGING APPARATUS AND METHOD OF CONTROLLING THE SAME

(71) Applicant: SAMSUNG ELECTRONICS CO., LTD., Suwon-si (KR)

(72) Inventor: Baeg Gi Mim, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 201 days.

(21) Appl. No.: 15/810,637

(22) Filed: Nov. 13, 2017

(65) Prior Publication Data
US 2018/0132812 A1     May 17, 2018

(30) Foreign Application Priority Data

Nov. 11, 2016  (KR) .................. 10-2016-0149967

(51) Int. Cl.
| | | |
|---|---|---|
| *A61B 6/00* | (2006.01) | |
| *A61B 8/08* | (2006.01) | |
| *G06T 11/00* | (2006.01) | |
| *A61B 6/03* | (2006.01) | |
| *A61B 6/04* | (2006.01) | |

(52) U.S. Cl.
CPC ............ *A61B 6/5258* (2013.01); *A61B 6/032* (2013.01); *A61B 6/0407* (2013.01); *A61B 6/40* (2013.01); *A61B 6/42* (2013.01); *A61B 6/461* (2013.01); *A61B 6/488* (2013.01); *A61B 6/5205* (2013.01); *A61B 6/54* (2013.01); *A61B 6/544* (2013.01); *A61B 6/563* (2013.01); *A61B 8/5207* (2013.01); *G06T 11/005* (2013.01)

(58) Field of Classification Search
None
See application file for complete search history.

(56) References Cited

U.S. PATENT DOCUMENTS

| | | |
|---|---|---|
| 2012/0114093 A1 | 5/2012 | Yu et al. |
| 2012/0155605 A1 | 6/2012 | Yazaki |
| 2013/0108130 A1 | 5/2013 | Nukui |

(Continued)

FOREIGN PATENT DOCUMENTS

| | | |
|---|---|---|
| JP | 2009-000522 A | 1/2009 |
| KR | 10-2006-0061249 A | 6/2006 |
| KR | 10-2014-0082721 A | 7/2014 |

OTHER PUBLICATIONS

Communication dated Apr. 6, 2018, issued by the European Patent Office in counterpart European Patent Application No. 17201284.1.

(Continued)

*Primary Examiner* — Hoon K Song
(74) *Attorney, Agent, or Firm* — Sughrue Mion, PLLC

(57) ABSTRACT

A medical imaging apparatus may include an image processor configured to generate an image based on data acquired by an X-ray detector, wherein the image processor determines a magnitude of a noise signal of a scout image of an object, determines a physical quantity of the object corresponding to the determined magnitude of the noise signal, determines an energy value of a monochromatic image by comparing the determined physical quantity of the object and a preset reference physical quantity, and generates the monochromatic image corresponding to the determined energy value.

18 Claims, 14 Drawing Sheets

(56) References Cited

U.S. PATENT DOCUMENTS

| | | |
|---|---|---|
| 2014/0363069 A1* | 12/2014 | Hsieh ................ G06T 5/005 |
| | | 382/131 |
| 2014/0376688 A1 | 12/2014 | Karmazyn et al. |
| 2015/0282778 A1 | 10/2015 | Kato et al. |
| 2015/0359501 A1 | 12/2015 | Eronen et al. |
| 2015/0359502 A1 | 12/2015 | Zou et al. |
| 2016/0157809 A1 | 6/2016 | Takahashi et al. |

OTHER PUBLICATIONS

Communication dated May 9, 2018, issued by the Korean Intellectual Property Office in counterpart Korean Patent Application No. 10-2016-0149967.

Communication dated Feb. 25, 2019, issued by the European Patent Office in counterpart European Application No. 17 201 284.1.

Communication dated Oct. 11, 2018, issued by the Korean Intellectual Property Office in corresponding Korean Application No. 10-2016-0149967.

* cited by examiner

FIG. 5
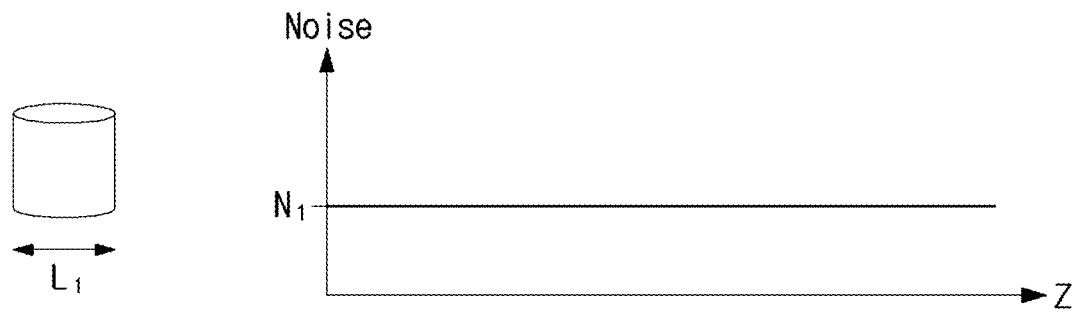
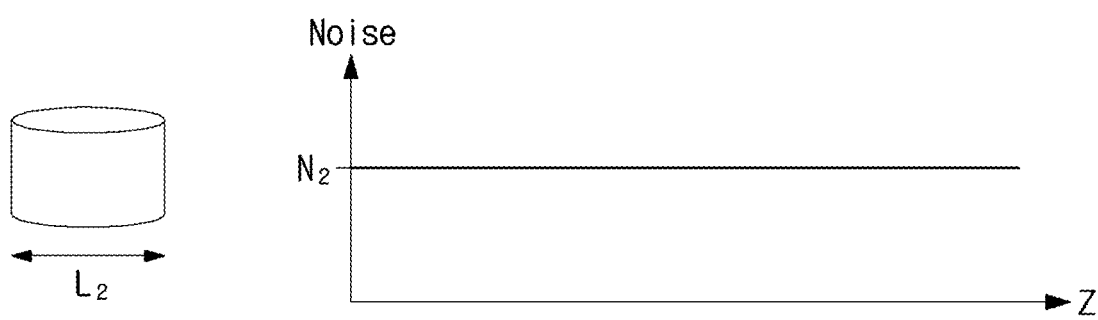
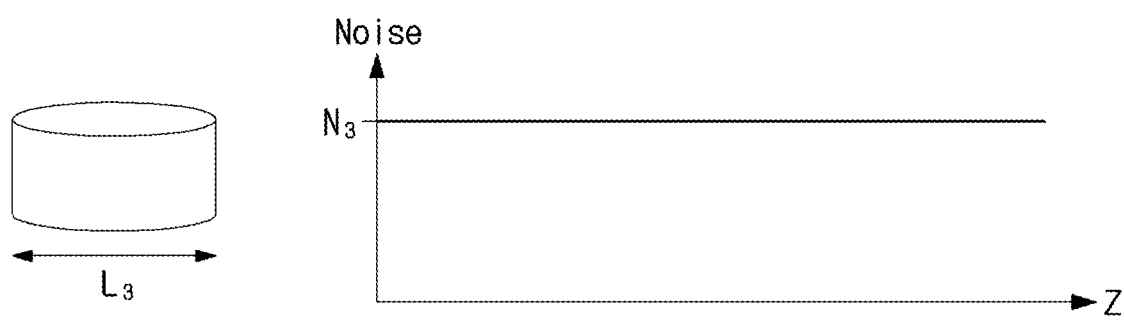

FIG. 6

| PHANTOM | PHYSICAL QUANTITY | | MAGNITUDE OF NOISE SIGNAL |
|---------|-------------------|---|---------------------------|
| WEP1 | $L_1$ | ⟷ | $N_1$ |
| WEP2 | $L_2$ | ⟷ | $N_2$ |
| WEP3 | $L_3$ | ⟷ | $N_3$ |
| | ⋮ | | |

FIG. 8
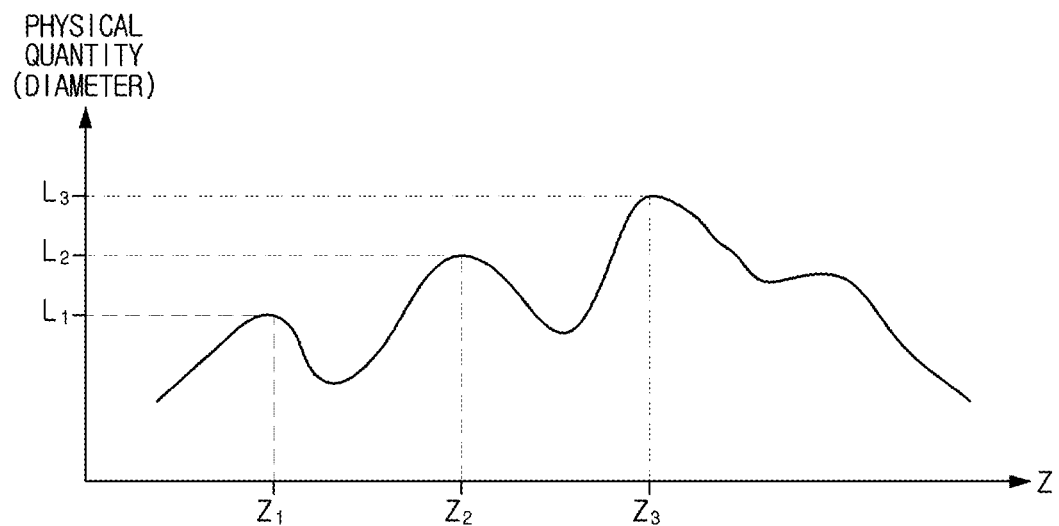
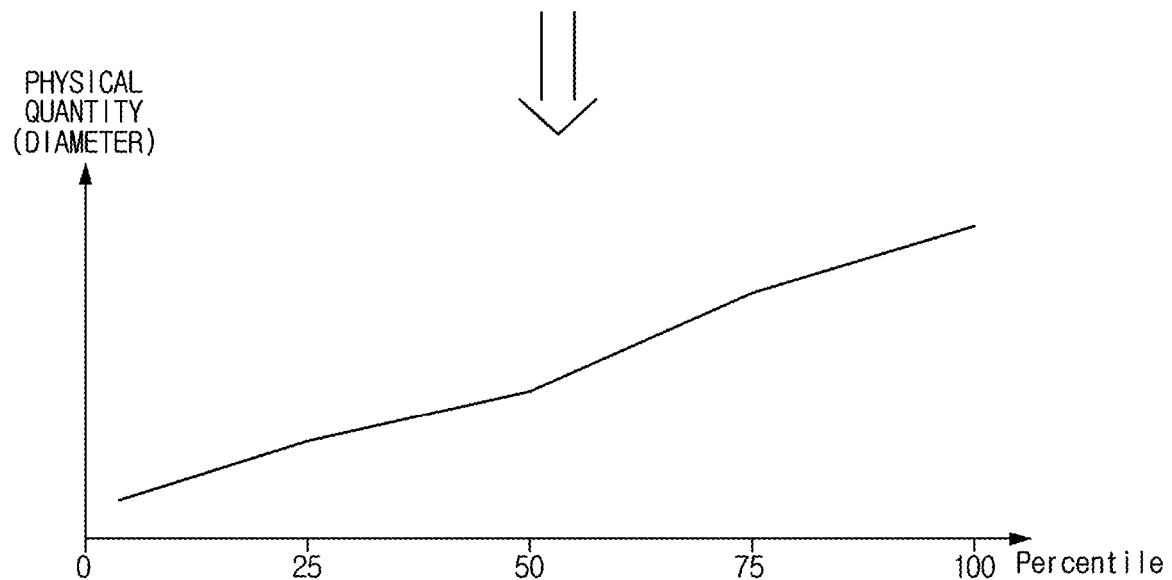

MEDICAL IMAGING APPARATUS AND METHOD OF CONTROLLING THE SAME

CROSS-REFERENCE TO RELATED APPLICATION(S)

This application claims the benefit of Korean Patent Application No. 10-2016-0149967, filed on Nov. 11, 2016 in the Korean Intellectual Property Office, the disclosure of which is incorporated herein by reference.

BACKGROUND

1. Field

Embodiments of the present disclosure relate to a medical imaging apparatus and a method of controlling the medical imaging apparatus.

2. Description of the Related Art

Medical imaging apparatuses are used to acquire images of an internal structure of an object. A medical image processing apparatus, as a non-invasive examination apparatus, acquires images of structural details of internal tissues, fluid streams, and the like of a human body, processes the acquired images, and displays the processed image to users. Users such as doctors may diagnose physical conditions and diseases of patients by using medical images output from the medical image processing apparatus.

A computed tomography (CT) apparatus is a representative imaging apparatus used to acquire an image of an object via irradiation of X-rays.

Among medical image processing apparatuses, a CT apparatus, which acquires sectional images, may provide an image of an object, i.e., an internal structure (e.g., an organ such as a kidney and a lung) of the object without an overlap therebetween. Thus, the CT apparatus has been widely used for accurate diagnosis of diseases. Hereinafter, a medical image acquired by a tomographic imaging apparatus will be referred to as a tomogram.

In order to acquire a tomogram, tomographic imaging is performed by a tomographic imaging apparatus and data is acquired therefrom. The tomographic imaging apparatus may reconstruct a tomogram of the object by using the acquired data.

A polychromatic imaging method for displaying a tomogram using various energy values or colors and a monochromatic imaging method for displaying a tomogram corresponding to one energy value are used as image reconstruction methods. Conventionally, a monochromatic image is reconstructed based on an energy value arbitrarily selected by a user based on the user's experiences without considering an optimal energy value.

SUMMARY

Therefore, it is an aspect of the present disclosure to provide a medical imaging apparatus to select an optimal energy value suitable for a patient's body and generate a monochromatic image corresponding to the selected energy value and a method of controlling the medical imaging apparatus.

Additional aspects of the disclosure will be set forth in part in the description which follows and, in part, will be obvious from the description, or may be learned by practice of the disclosure.

One aspect of the present disclosure provides a medical imaging apparatus. The medical imaging apparatus may comprise an image processor configured to generate an image based on data acquired by an X-ray detector; and a display configured to display the image, wherein the image processor determines a magnitude of a noise signal of a scout image of an object, determines a physical quantity of the object corresponding to the determined magnitude of the noise signal, determines an energy value of a monochromatic image by comparing the determined physical quantity of the object and a preset reference physical quantity, and generates the monochromatic image corresponding to the determined energy value.

The image processor may determine magnitudes of noise signals of the object on the basis of regions, determines physical quantities of the object on the basis of regions corresponding to the magnitudes of the noise signals of the object on the basis of regions, and determines the energy value of the monochromatic image by comparing a representative value of the determined physical quantities of the object on the basis of regions with a preset reference physical quantity.

The image processor may select a physical quantity having a preset magnitude ratio as a representative value of the physical quantities on the basis of regions.

The image processor may increase the energy value when the determined physical quantity of the object is equal to or greater than the preset reference physical quantity and decreases the energy value when the determined physical quantity of the object is less than the preset reference physical quantity.

The image processor may determine the degree of the energy value to be increased or decreased in proportional to a difference value between the determined physical quantity of the object and the preset reference physical quantity.

The medical imaging apparatus may comprise an input unit configured to input the energy value, wherein the image processor generates a monochromatic image corresponding to the energy value input via the input unit.

The input unit may receive an instruction to enter an automatic mode or a manual mode, and the image processor generates a monochromatic image corresponding to the determined energy value when the input unit receives the instruction to enter the automatic mode and generates a monochromatic image corresponding to the input energy value when the input unit receives the instruction to enter the manual mode.

The physical quantities on the basis of regions may comprise a diameter of a cross-section or a volume of the object shown in the scout image.

The medical imaging apparatus may comprise a gantry comprising an X-ray generator configured to emit X-rays and an X-ray detector configured to detect X-rays generated by the X-ray generator and received through the object; and a table on which the object is positioned and configured to move into and out of the gantry.

The image processor may generate a plurality of scout images in one direction of the object based on data acquired by the X-ray detector, and the image processor determines magnitudes of noise signals of the plurality of scout images as the magnitudes of the noise signals of the object on the basis of regions.

The one direction may be a direction in which the table moves into and out of the gantry.

The medical imaging apparatus may comprise a computed tomography imaging apparatus.

Another aspect of the present disclosure provides a method of controlling a medical imaging apparatus. The method may comprise generating a scout image of an object based on data acquired by an X-ray detector; determining a magnitude of a noise signal of the scout image; determining a physical quantity of the object corresponding to the determined magnitude of the noise signal; determining an energy value of a monochromatic image by comparing the determined physical quantity of the object with a pre-stored reference physical quantity; and generating a monochromatic image corresponding to the determined energy value.

The determining of the magnitude of the noise signal may be performed by determining magnitudes of the noise signals of the object on the basis of regions, the determining of the physical quantity of the object may be performed by determining physical quantities of the object on the basis of regions corresponding to the magnitudes of the noise signals of the object on the basis of regions, and the determining of energy value of the monochromatic image may be performed by determining an energy value of a monochromatic image by comparing a representative value of the determined physical quantities of the object on the basis of regions with a preset reference physical quantity.

The determining of the energy value of the monochromatic image may comprise selecting a physical quantity having a preset magnitude ratio as a representative value of the physical quantities on the basis of regions.

The determining of the energy value of the monochromatic image may be performed by increasing the energy value when the determined physical quantity of the object is equal to or greater than the preset reference physical quantity and decreasing the energy value when the determined physical quantity of the object is less than the preset reference physical quantity.

The determining of the energy value of the monochromatic image may comprise determining the degree of the energy value to be increased or decreased in proportional to a difference between the determined physical quantity of the object and the preset reference physical quantity.

The generating of the scout image of the object may be performed by generating a plurality of scout images in one direction of the object, and the determining of the magnitude of the noise signal of the scout image is performed by determining magnitudes of noise signals of the plurality of scout images as the magnitudes of the noise signals of the object on the basis of regions.

The medical imaging apparatus may comprise a gantry configured to emit and detect X-rays and a table on which the object is positioned and configured to move into and out of the gantry, and the one direction is a direction in which the table moves into and out of the gantry.

The method may further comprise storing a mapping table comprising physical quantities and magnitudes of noise signals based on cross-sectional images of a phantom before receiving data, wherein the determining of the physical quantity of the object is performed by determining physical quantities of the object corresponding to the determined magnitudes of the noise signals based on the mapping table.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 5 illustrates noise signal graphs of phantoms for describing a process of creating a mapping table used to convert the magnitudes of noise signals into the physical quantities.

FIG. 6 is an exemplary mapping table created thereby.

FIG. 8 is a graph for describing a process of arranging physical quantities of regions of an object in the order of magnitude.

DETAILED DESCRIPTION

Figure 1:
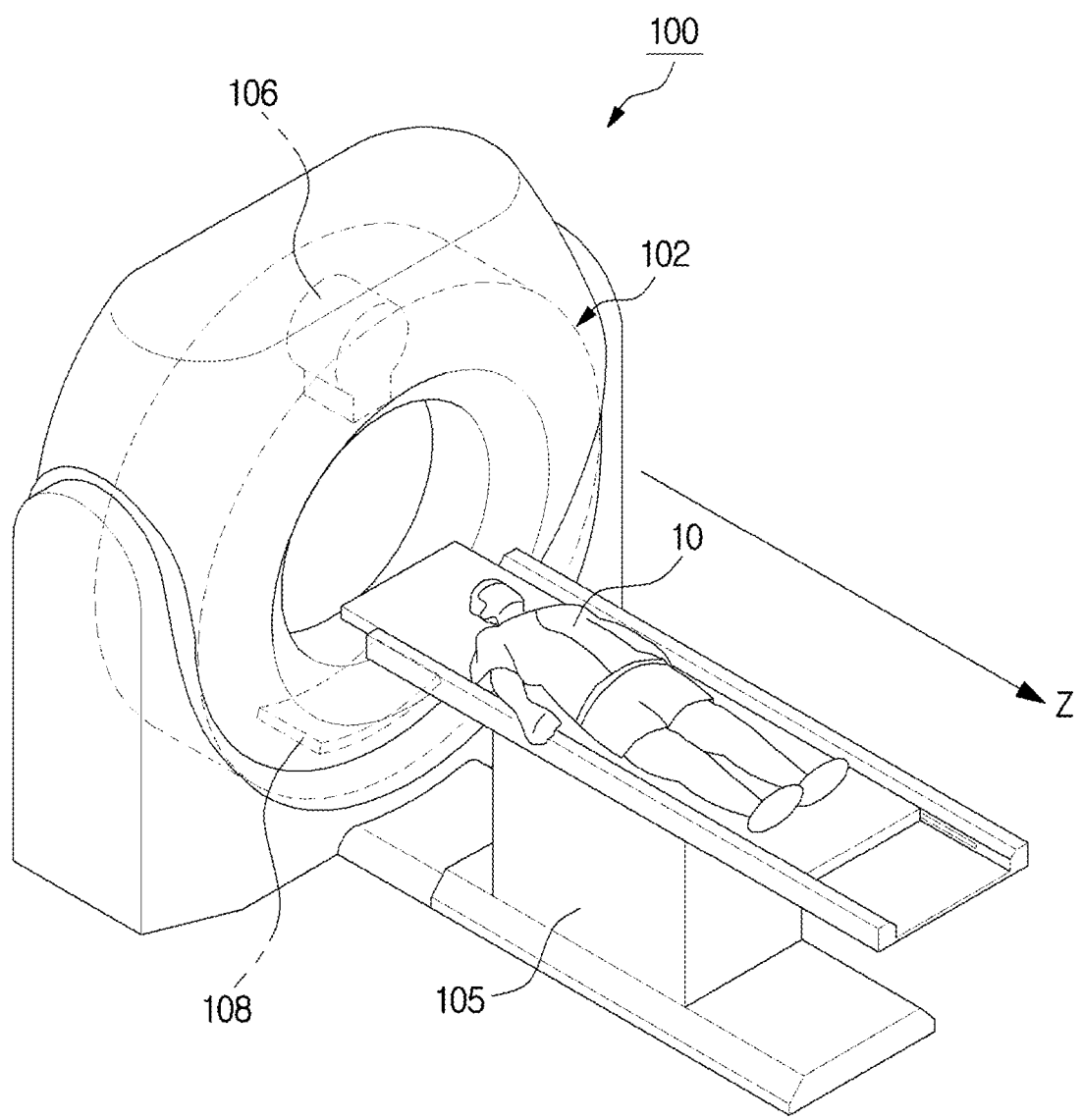
FIG. 1 is a schematic view illustrating a conventional CT apparatus.

Reference will now be made in detail to the embodiments of the present disclosure, examples of which are illustrated in the accompanying drawings, wherein like reference numerals refer to like elements throughout. This specification does not describe all elements of the embodiments of the present disclosure and detailed descriptions on what are well known in the art or redundant descriptions on substantially the same configurations may be omitted. The terms 'unit, module, member, or block' used herein may be implemented using a software or hardware component. According to an embodiment, a plurality of 'units, modules, members, or blocks' may also be implemented using an element and one 'unit, module, member, or block' may include a plurality of elements.

Throughout the specification, when an element is referred to as being "connected to" another element, it may be directly or indirectly connected to the other element and the "indirectly connected to" includes connected to the other element via a wireless communication network.

Also, it is to be understood that the terms "include" or "have" are intended to indicate the existence of elements disclosed in the specification, and are not intended to preclude the possibility that one or more other elements may exist or may be added.

In this specification, terms "first," "second," etc. are used to distinguish one component from other components and, therefore, the components are not limited by the terms.

An expression used in the singular encompasses the expression of the plural, unless it has a clearly different meaning in the context.

The reference numerals used in operations are used for descriptive convenience and are not intended to describe the order of operations and the operations may be performed in a different order unless otherwise stated.

Hereinafter, embodiments of the present disclosure will be described in detail with reference to the accompanying drawings.

Throughout the specification, an "image" may refer to multi-dimensional data formed of discrete image elements (e.g., pixels in a two-dimensional (2D) image and voxels in a three-dimensional (3D) image). For example, the image may include a medical image of an object acquired by a computed tomography (CT) imaging apparatus.

Throughout the specification, a "CT image" or "tomogram" may refer to an image synthesized using a plurality of X-ray images acquired by photographing an object while a CT imaging apparatus rotates about at least one axis with respect to the object.

Throughout the specification, an "object" may refer to a human, an animal, or a part of a human or animal. For example, the object may include at least one of organs such as liver, heart, womb, brain, breast, and abdomen and blood vessels. Also, the "object" may be a phantom. The phantom refers to a material having a volume very close to a density and effective atomic number of an organism and may include a sphere phantom having characteristics similar to those of a human body. The phantom may also include an image quality evaluation phantom used to evaluate image quality and a calibration phantom used to estimate point spread function (PSF).

As used herein, a "user" may refer to a medical professional, such as a doctor, a nurse, a medical laboratory technologist, a medical imaging professional, and a medical equipment technician, and the like, without being limited thereto.

A medical imaging apparatus 100 may include any imaging apparatuses that acquire tomograms such as a computed tomography (CT) apparatus, an optical coherence tomography (OCT) apparatus, and a positron emission tomography (PET)-CT apparatus.

Hereinafter, a CT apparatus will be described as an example of the medical imaging apparatus 100.

Since a CT apparatus 100 is capable of providing cross-sectional images of an object, the CT apparatus 100 may express an inner structure (e.g., an organ such as a kidney and a lung) of the object without an overlap between discrete portions of the object, compared to a conventional X-ray imaging apparatuses.

The CT apparatus 100 may acquire a plurality of image data each with a thickness of 2 mm or less for several tens to several hundreds of times per second and then process the acquired data, thereby providing a relatively accurate cross-sectional image of the object. Although only horizontal cross-sectional images of the object have been acquired according to the related art, this issue has been overcome due to various image construction methods below. Examples of 3D image reconstruction methods are as follows.

Shade Surface Display (SSD): An initial imaging method that displays only voxels having a predetermined Hounsfield Unit (HU) value.

Maximum Intensity Projection (MIP)/Minimum Intensity Projection (MinIP): A 3D imaging method that displays only voxels having the highest or lowest HU value among voxels constructing an image.

Volume Rendering (VR): An imaging method capable of adjusting color and transmittance of voxels on the basis of region of interest that construct an image.

Virtual Endoscopy: A method allowing endoscopic observation in a 3D image reconstructed by VR or SSD methods.

Multi Planar Reformation (MPR): A method of reconstructing an image into a different cross-sectional image. A user may reconstruct an image in a desired direction.

Editing: A method of editing adjacent voxels so as to allow a user to easily observe a region of interest in volume rendering.

Voxel of Interest (VOI): A method of displaying only a selected area in volume rendering.

A CT apparatus 100 according to an embodiment will be described with reference to FIG. 1. The CT apparatus 100 may include apparatuses in various shapes.

FIG. 1 is a schematic view illustrating a conventional CT apparatus.

Referring to FIG. 1, the CT apparatus 100 may include a gantry 102, a table 105, an X-ray generator 106, and an X-ray detector 108.

The gantry 102 may include the X-ray generator 106 and the X-ray detector 108.

The object 10 may be positioned on the table 105.

The table 105 may move in a predetermined direction (e.g., at least one of up and down-right and left directions) during a CT imaging procedure. Also, the table 105 may tilt or rotate by a predetermined angle in a given direction. Hereinafter, a direction in which the table 105 moves into and out of the gantry 102 is referred to as a Z-axis direction for descriptive convenience. In FIG. 1, a direction in which the object 10 is lying is the Z-axis direction.

Also, the gantry 102 may tilt by a predetermined angle in a given direction.

Figure 2:
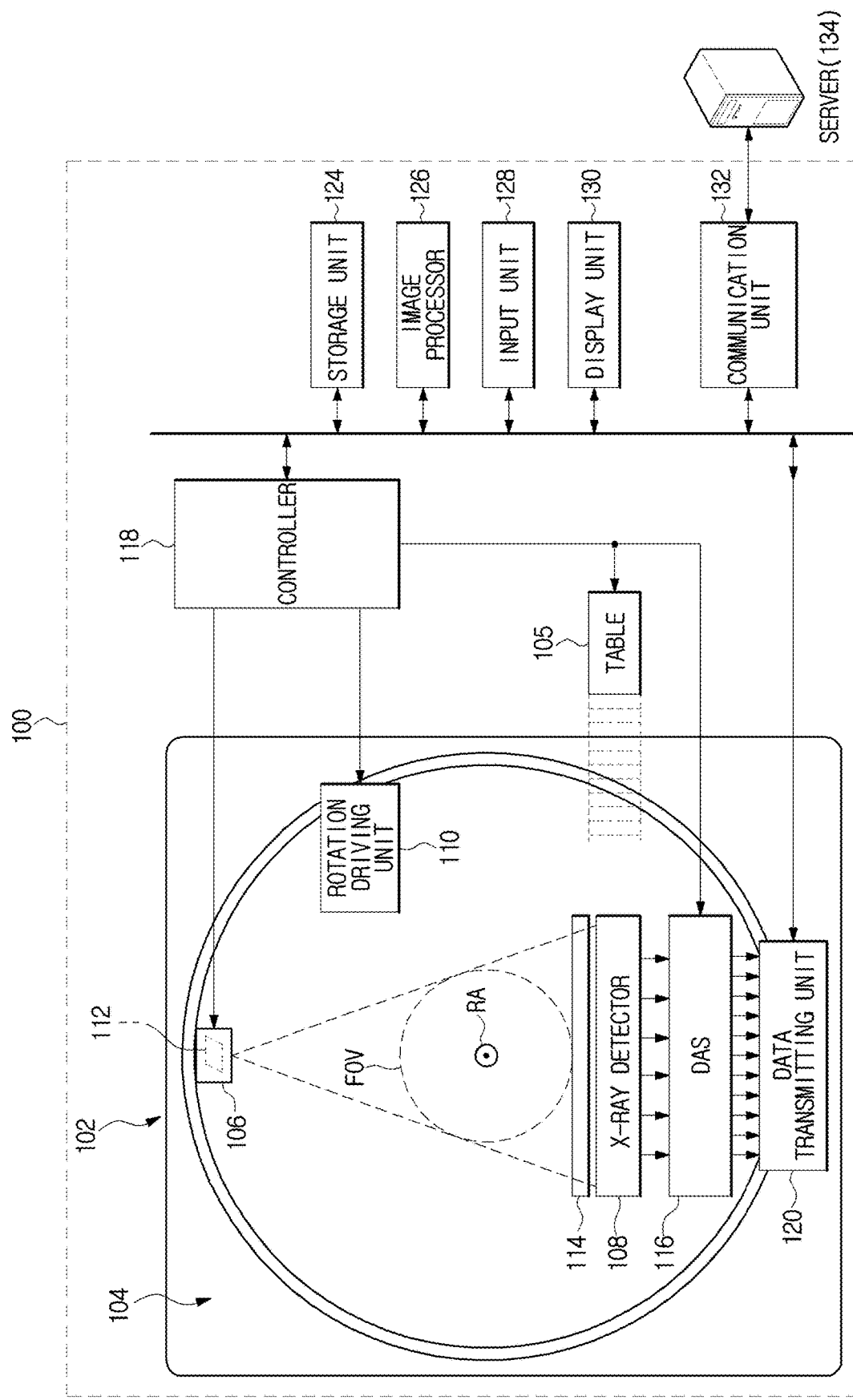
FIG. 2 is a diagram illustrating a structure of a CT apparatus 100 according to an embodiment of the present disclosure.

FIG. 2 is a diagram illustrating a structure of a CT apparatus 100 according to an embodiment of the present disclosure.

The CT apparatus 100 according to the present embodiment may include a gantry 102, a table 105, a controller 118, a storage unit 124, an image processor 126, an input unit 128, a display unit 130, and a communication unit 132.

As described above, an object 10 may be positioned on the table 105. The table 105 according to the present embodiment may move in a predetermined direction (e.g., at least one of up and down-right and left directions), and movement of the table 105 may be controlled by the controller 118.

The gantry 102 may include a rotating frame 104, an X-ray generator 106, an X-ray detector 108, a rotation driving unit 110, a data acquisition system (DAS) 116, and a data transmitting unit 120.

The gantry 102 may include the rotating frame 104 having a loop shape and rotatable with respect to a predetermined rotation axis (RA). Also, the rotating frame 104 may have a disc shape.

The rotating frame 104 may have the X-ray generator 106 and the X-ray detector 108 that face each other to have predetermined fields of view (FOVs). The rotating frame 104 may further include an anti-scatter grid 114. The anti-scatter grid 114 may be disposed between the X-ray generator 106 and the X-ray detector 108.

X-ray radiation that arrives at a detector (or photosensitive film) includes not only attenuated primary radiation that forms a valuable image but also scattered radiation that deteriorates the quality of image. In order to transmit most of the primary radiation and attenuate the scattered radiation, the anti-scatter grid 114 may be disposed between a patient and the detector (or photosensitive film).

For example, the anti-scatter grid 114 may be formed by alternately stacking strips of lead foil and an interspace material such as a non-porous solid polymer material or a fiber composite material. However, the structure of the anti-scatter grid 114 is not limited thereto.

The rotating frame 104 may receive a driving signal from the rotation driving unit 110 and rotate the X-ray generator 106 and the X-ray detector 108 at a predetermined rotation speed. The rotating frame 104 may receive the driving signal and power from the rotation driving unit 110 while the rotating frame 104 contacts the rotation driving unit 110 via a slip ring (not shown). Also, the rotating frame 104 may receive the driving signal and power from the rotation driving unit 110 via a wireless communication network.

The X-ray generator 106 may generate and emit X-rays by receiving a voltage or current from a power distribution unit (PDU) (not shown) via a slip ring (not shown) and then a high voltage generating unit (not shown). When the high voltage generating unit applies a predetermined voltage (hereinafter, referred to as tube voltage) to the X-ray generator 106, the X-ray generator 106 may generate X-rays having a plurality of energy spectra that correspond to the tube voltage.

X-rays generated by the X-ray generator 106 may be emitted in a predetermined form or into a predetermined region by a collimator 112.

The X-ray detector 108 may be positioned to face the X-ray generator 106. The X-ray detector 108 may include a plurality of X-ray detecting elements. Although each of the plurality of X-ray detecting elements may establish one channel, the embodiments of the present disclosure are not limited thereto.

The X-ray detector 108 may detect X-rays generated by the X-ray generator 106 and received through the object 10 and generate electrical signals corresponding to the intensity of the detected X-rays.

The X-ray detector 108 may include an indirect-type X-ray detector configured to detect radiation after converting the radiation into light and a direct-type X-ray detector configured to detect radiation after directly converting the radiation into electric charges. A scintillator may be used as the indirect-type X-ray detector. In addition, a photon counting detector may be used as the direct-type X-ray detector.

The DAS 116 may be connected to the X-ray detector 108. The electrical signals generated by the X-ray detector 108 may be collected by the DAS 116 in a wired or wireless manner.

In addition, the electrical signals generated by the X-ray detector 108 may be provided to an analog/digital converter (not shown) via an amplifier (not shown).

Only some of a plurality of pieces of data collected from the X-ray detector 108 may be provided to the image processor 126 according to a slice thickness or the number of slices. Also, the image processor 126 may select only some of the plurality of pieces of data.

Such digital signals may be provided to the image processor 126 via the data transmitting unit 120. The digital signals may be transmitted to the image processor 126 in a wired or wireless manner via the data transmitting unit 120.

The controller 118 may control the operation of each of the modules of the CT apparatus 100. For example, the controller 118 may control the operation of the table 105, the rotation driving unit 110, the collimator 112, the DAS 116, the storage unit 124, the image processor 126, the input unit 128, the display unit 130, the communication unit 132, or the like.

The controller 118 may be implemented using a memory (not shown) that stores data on algorithms to control the operation of each of the modules of the CT apparatus 100 or data on programs to run the algorithms and a processor (not shown) that performs the aforementioned operation by using data stored in the memory. In this case, the memory and the processor may be implemented as separate chips. Alternatively, the memory and the processor may be implemented as a single chip.

The image processor 126 may receive data (e.g., pure data before processing), which is acquired from the DAS 116, via the data transmitting unit 120, and may perform pre-processing.

The pre-processing may include a process of correcting sensitivity irregularity between channels, a process of correcting a signal loss due to a rapid decrease of a signal strength or due to an X-ray absorbing material such as metal, or the like.

Data output from the image processor 126 may be referred to as raw data or projection data. The projection data and image capturing conditions (e.g., tube voltage and image capturing angle) while acquiring data may be stored together in the storage unit 124.

The projection data may be a group of data values corresponding to the intensities of the X-rays that pass through the object. For descriptive convenience, a group of a plurality of pieces of projection data that are simultaneously obtained from all channels in the same imaging angle is referred to as a projection data set.

The storage unit 124 may include at least one type of storage medium selected from a flash memory type storage medium, a hard disk type storage medium, a multimedia card micro type storage medium, a card type memory (e.g., SD card and XD memory), Random Access Memory (RAM), Static Random Access Memory (SRAM), Read-Only Memory (ROM), Electrically Erasable Programmable Read-Only Memory (EEPROM), Programmable Read-Only Memory (PROM), a magnetic memory, a magnetic disc, and an optical disc.

The storage unit 124 and the controller 118 may be implemented as a single chip or separate chips.

The image processor 126 may generate a primary cross-sectional image using the acquired projection data set and generate a second cross-sectional image of the object by reconstructing the primary cross-sectional image. The secondary cross-sectional image may be a 3D image. In other words, the image processor 126 may generate a 3D image of the object by cone beam reconstruction based on the acquired projection data set.

The image processor 126 may determine magnitudes of noise signals of the object on the basis of regions of the object based on scout images of the respective regions of the object and determine physical quantities of the object corresponding to the determined magnitudes of the noise signals on the basis of regions of the object.

In this regard, the magnitudes of the noise signals of the object on the basis of regions refer to magnitudes of noise signals of a plurality of cross-sectional images in the Z-axis direction in which the object moves into and out of the gantry and the physical quantities of the object on the basis of regions refer to physical quantities of the plurality of cross-sectional images in the Z-axis direction.

In addition, the scout image refers to a primary cross-sectional image acquired when the same amount of X-rays is irradiated to the object, and the physical quantities of the object on the basis of regions may be various values representing a body size of the object such as a diameter, thickness, cross-sectional area, and volume of the object shown by the primary cross-sectional image.

Particularly, a plurality of scout images of the object, each acquired when the same amount of X-rays is irradiated to the object, may be acquired while the table 105 moves in the Z-axis direction and each of the plurality of scout images includes information on the noise signal.

The image processor 126 acquires scout images of a plurality of regions of the object in the Z-axis direction, determines magnitudes of noise signals of the respective scout images, and determines physical quantities of the object on the basis of regions corresponding to the determined magnitudes of the respective noise signals of the scout images based on a pre-stored mapping table. The mapping table will be described later.

In addition, the image processor 126 determines an energy value of a monochromatic image by comparing physical quantities of the respective regions of the scout images with pre-stored reference values and generates a monochromatic image corresponding the determined energy value as a secondary cross-sectional image.

The monochromatic image is an image reconstructed by a monochromatic imaging method that extracts a cross-sectional image having a given energy value or wavelength.

The operation of the image processor 126 will be described below in more detail.

The image processor 126 may be implemented using a memory that stores data on algorithms to convert digital data into an image or perform image processing or data on programs to run the algorithms and a graphics processing unit (GPU) that performs the aforementioned operation by using the data stored in the memory. In this case, the memory and the GPU may be implemented as separate chips. Alternatively, the memory and the GPU may be implemented as a single chip.

The image processor 126 may be integrated with the controller 118 or the storage unit 124 as a single chip or may be configured as a separate chip.

Via the input unit 128, an external input with respect to X-ray tomography imaging conditions, image processing conditions, and the like may be received. For example, the X-ray tomography imaging conditions may include a plurality of tube voltages, energy value settings with respect to a plurality of X-rays, selection of an image capturing protocol, selection of an image reconstruction method, setting of a field of view (FOV) area, the number of slices, a slice thickness, parameter setting with respect to post-processing of image, and the like. Also, the image processing conditions may include resolution of an image, attenuation coefficient setting with respect to the image, setting of an image combining ratio, and the like.

When the user desires to receive a monochromatic image, the input unit 128 may receive an instruction to enter an automatic mode or a manual mode from the user. Upon receiving the instruction to enter the automatic mode, the image processor 126 automatically determines an energy value of the monochromatic image and reconstructs an image. However, upon receiving the instruction to enter the manual mode, the image processor 126 generates a monochromatic image corresponding to an energy value input by the user.

The input unit 128 may include a device for receiving a predetermined input from an external source. For example, the input unit 128 may include a microphone, a keyboard, a mouse, a joystick, a touch pad, a touch pen, a voice recognition device, a gesture recognition device, or the like.

The display unit 130 may display an X-ray tomographic image reconstructed by the image processor 126.

The display unit 130 may display a monochromatic image generated by the image processor 126.

Exchanges of data, power, or the like between the aforementioned elements may be performed via at least one of wired, wireless, and optical communication networks.

The communication unit 132 may perform communication with an external device, an external medical apparatus, or the like via a server 134, or the like. This will be described below with reference to FIG. 3.

Figure 3:
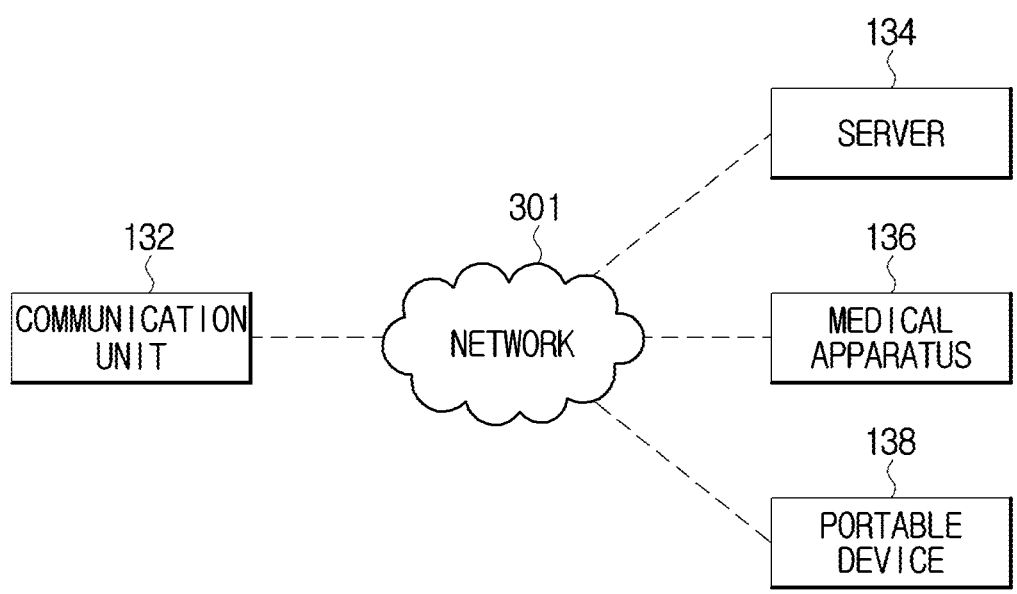
FIG. 3 is a diagram illustrating a structure of the communication unit.

FIG. 3 is a diagram illustrating a structure of the communication unit.

The communication unit 132 may be connected to a network 301 in a wired or wireless manner and perform communication with the server 134, an external medical apparatus 136, or an external portable device 138. The communication unit 132 may exchange data with a hospital server or other medical apparatuses in a hospital via a picture archiving and communication system (PACS).

In addition, the communication unit 132 may perform data communication with the portable device 138 or the like according to a Digital Imaging and Communications in Medicine (DICOM) standard.

The communication unit 132 may transmit and receive data related to diagnosis of the object via the network 301. In addition, the communication unit 132 may transmit and receive a medical image acquired by the medical apparatus 136 such as an MRI apparatus and an X-ray apparatus.

Furthermore, the communication unit 132 may receive a diagnosis history or a medical treatment schedule of a patient from the server 134 and use the diagnosis history or the medical treatment schedule in a clinical diagnosis of the patient. In addition, the communication unit 132 may perform data communication with not only the server 134 or the medical apparatus 136 in a hospital but also with the portable device 138 of the user or patient.

Also, the communication unit 132 may transmit information on malfunction, a quality management status, or the like to a system manager or a service manager via the network and may receive feedback corresponding to the information.

Components may be added or deleted corresponding to performance of the components of the CT apparatus 100 illustrated in FIGS. 1 to 3. In addition, it will be readily understood by those skilled in the art that mutual positions of the components may be changed to correspond to performance or structure of a system.

Meanwhile, some of the elements illustrated in FIGS. 1 to 3 may be software and/or hardware components such as a Field Programmable Gate Array (FPGA) or an Application Specific Integrated Circuit (ASIC).

Hereinafter, the operation of the image processor 126 will be described in detail with reference to FIGS. 4A to 9.

Figure 4A:
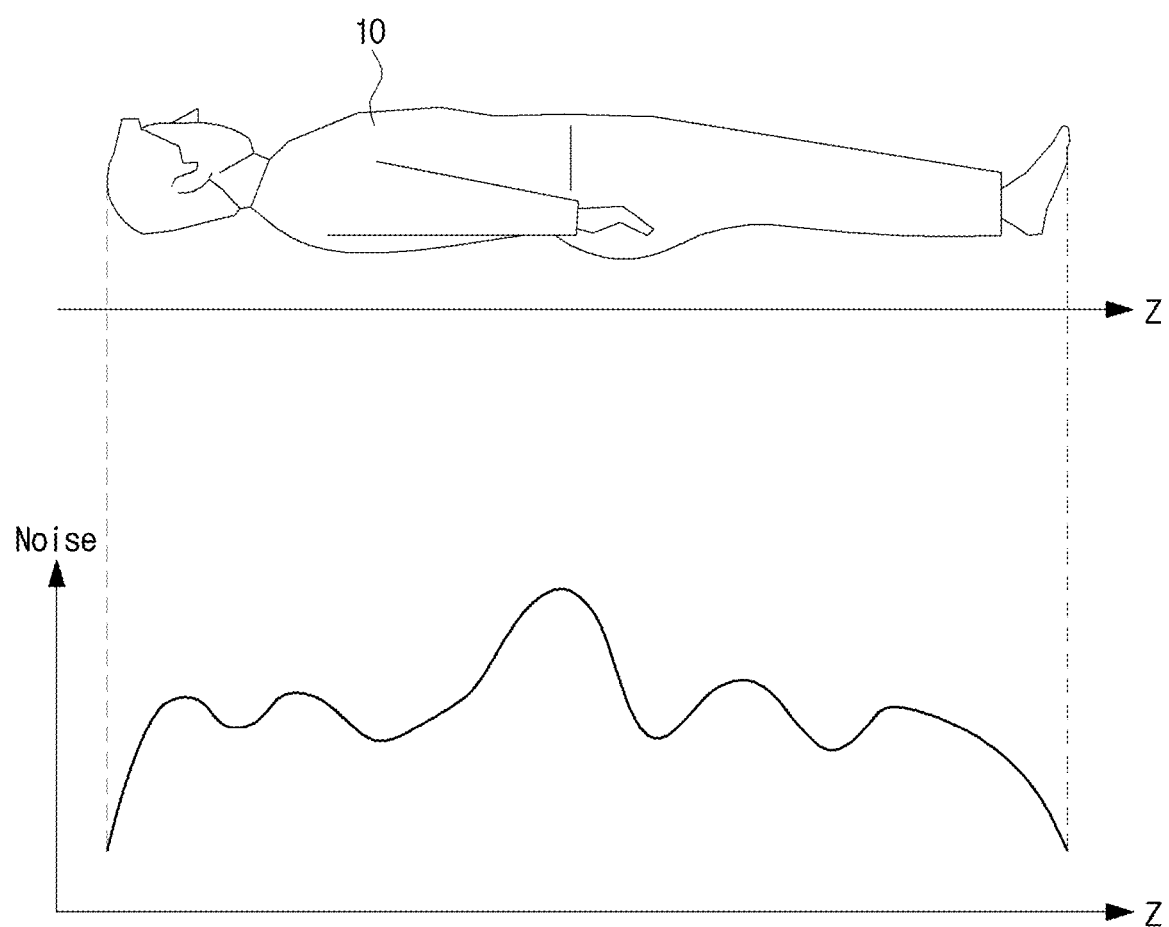
FIGS. 4A and 4B are graphs illustrating an object and magnitudes of noise signals of the object in a Z-axis direction.
Figure 4B:
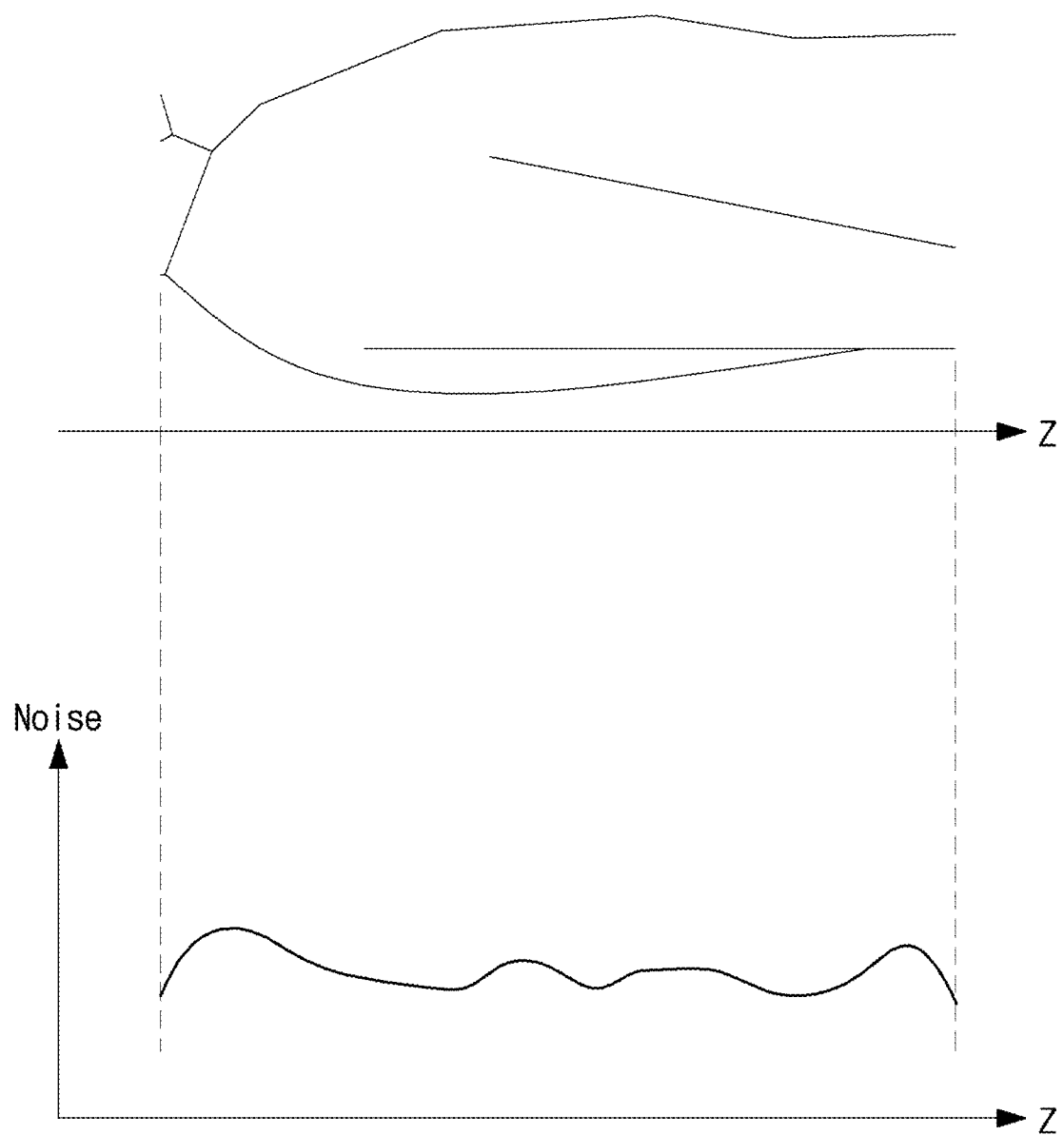

FIGS. 4A and 4B are graphs illustrating an object and magnitudes of noise signals of the object in a Z-axis direction.

Referring to FIG. 4A, when the object is the entire body of a patient and the patient is lying in the Z-axis direction as an example, a plurality of cross-sectional images may be acquired from the head to the toe of the patient and each of the cross-sectional images includes a noise signal.

The image processor 126 according to an embodiment may determine magnitudes of noise signals of the plurality of cross-sectional images and calculate magnitudes of the noise signals of the object on the basis of regions of the object in the Z-axis direction as illustrated in FIG. 4A.

Referring to FIG. 4B, when the object is a part of the body of a patient as another example, a plurality of cross-sectional images may be acquired from a chest to a waist and each of the cross-sectional image includes a noise signal.

The image processor 126 may determine magnitudes of noise signals of the plurality of cross-sectional images and calculate magnitudes of the noise signals of the object on the basis of regions of the object in the Z-axis direction as illustrated in FIG. 4B.

Figure 7:
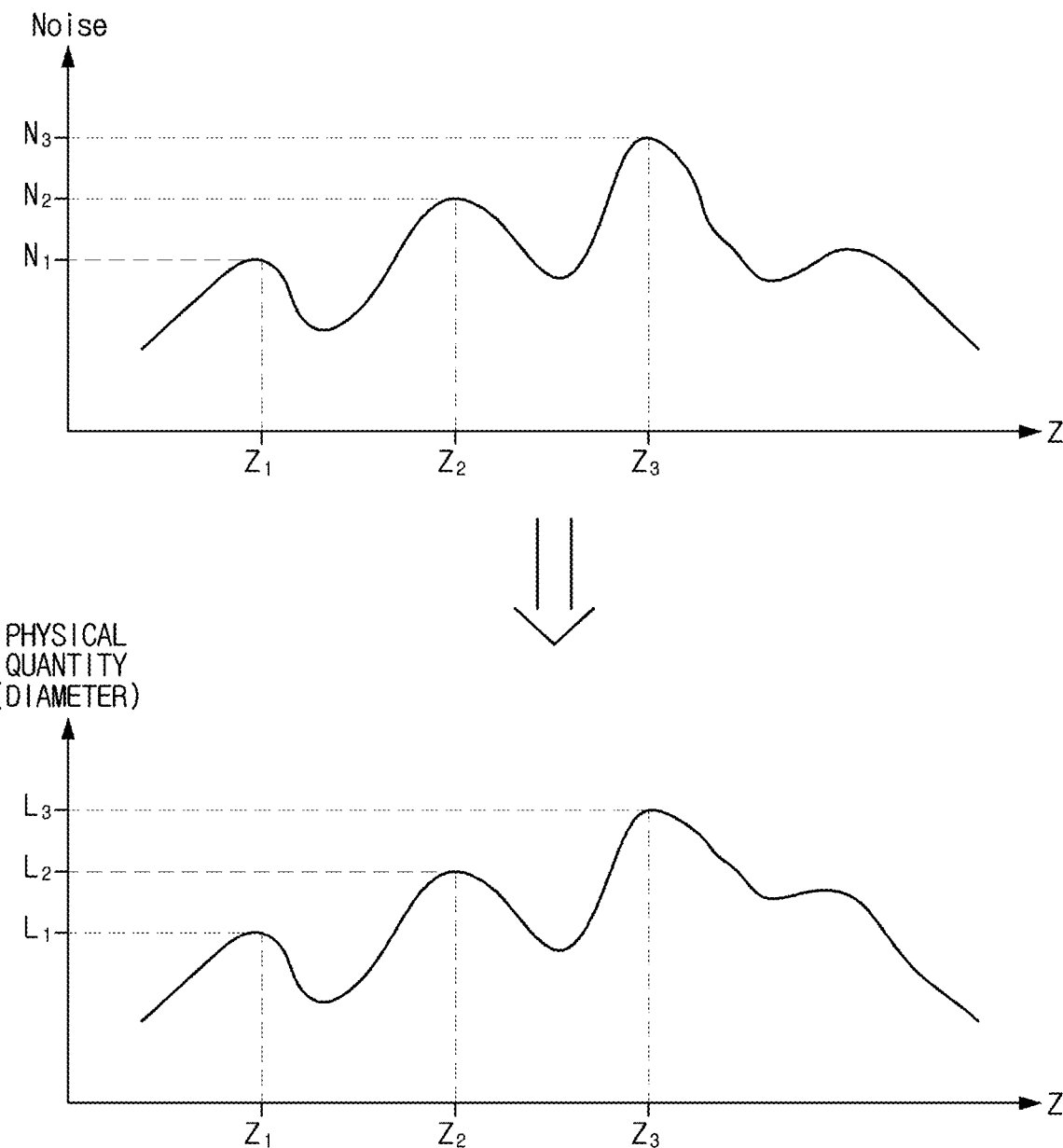
FIG. 7 is a graph for describing a process of converting magnitudes of noise signals into physical quantities by using the mapping table.

The calculated magnitudes of the noise signals of the object on the basis of regions of the object may be converted into physical quantities by the image processor 126. FIG. 5 illustrates noise signal graphs of phantoms for describing a process of creating a mapping table used to convert the magnitudes of noise signals into the physical quantities corresponding to the phantoms. FIG. 6 is an exemplary mapping table created thereby. FIG. 7 is a graph for describing a process of converting magnitudes of noise signals into physical quantities by using the mapping table.

Referring to FIG. 5, the image processor 126 may acquire cross-sectional images of phantoms having different diameters L1, L2, and L3 and calculate magnitudes of noise signals N1, N2, and N3 included in the cross-sectional images before acquiring scout images of the object. In this case, the cross-sectional image may be a scout image of a phantom and a method of calculating a magnitude of a noise signal from a cross-sectional image may be well known in the art and thus detailed descriptions thereof will not be repeated. The phantom may be a water equivalent phantom (WEP) and it is assumed that magnitudes of noise signals on the basis of regions of one phantom in the Z-axis direction are the same.

Thus, if it is assumed that the magnitudes of the noise signals N1, N2, and N3 of the plurality of phantoms having different diameters are different from each other, the phantoms may be identified by information on the magnitudes of the noise signals and the diameters of the phantoms may also be estimated.

To this end, referring to FIG. 6, the image processor 126 stores magnitudes of noise signals N1, N2, and N3 corresponding to diameters L1, L2, and L3 of a plurality of phantoms WEP1, WEP2, and WEP3 in a mapping table. The mapping table may be stored in the memory of the image processor 126 or the storage unit 124. The diameters L1, L2, and L3 of the plurality of phantoms WEP1, WEP2, and WEP3 may be values input by the user via the input unit 128 or acquired by the controller 118 or the image processor 126 via tags attached to or chips embedded in the phantoms WEP1, WEP2, and WEP3, respectively.

Referring to FIG. 7, the image processor 126 may acquire scout images of the object, calculate the magnitudes of the noise signals of the respective regions of the object in the Z-axis direction based on the scout images, and convert the magnitudes of the noise signals into physical quantities (i.e., diameters) of the object based on the mapping table.

Although the number of the phantoms WEP1, WEP2, and WEP3 stored in the mapping table is limited in some embodiments, the image processor 126 may estimate a diameter of another phantom based on the magnitudes of the noise signals N1, N2, and N3 corresponding to the pre-stored diameters L1, L2, and L3 of the plurality of phantoms WEP1, WEP2, and WEP3.

For example, in a cross-sectional image of a region of the object having a noise signal, the magnitude of which is greater than that of a noise signal N1 of a first phantom WEP1 and smaller than that of a noise signal N2 of a second phantom WEP2, the image processor 126 may estimate that the region has a diameter greater than the diameter L1 of the first phantom WEP1 and smaller than the diameter L2 of the second phantom WEP2.

When the diameter is proportional to the magnitude of the noise signal, the graph of diameters of the object on the basis of regions may have the same shape of the graph of magnitudes of the noise signals of the object on the basis of regions as illustrated in FIG. 7.

Figure 9:
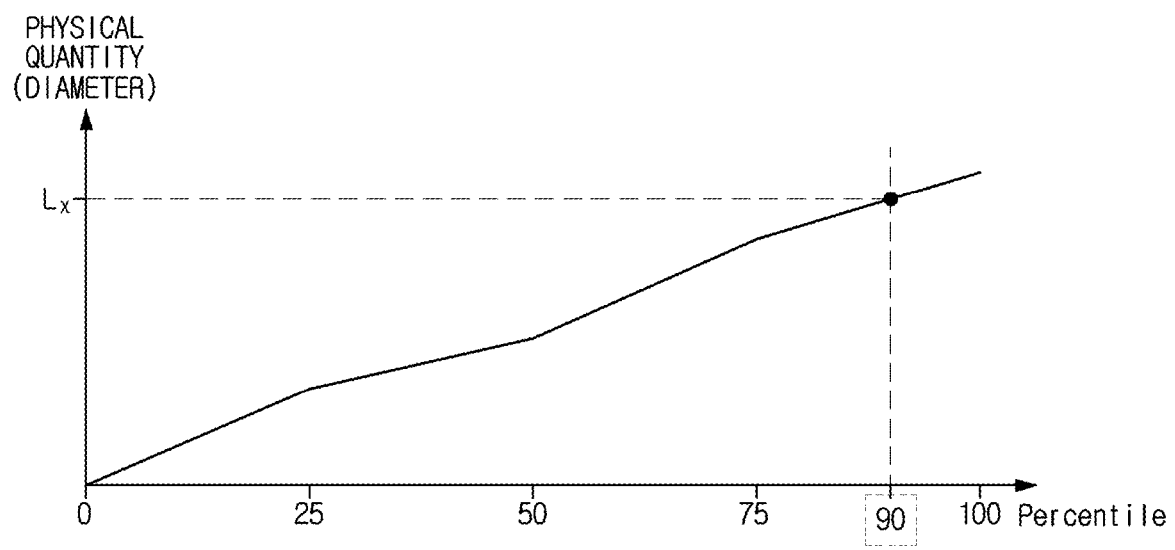
FIG. 9 is a graph for describing a process of selecting one of physical quantities arranged in the order of magnitude.

FIG. 8 is a graph for describing a process of arranging physical quantities of regions of an object in the order of magnitude. FIG. 9 is a graph for describing a process of selecting one of physical quantities arranged in the order of magnitude.

The image processor 126 determines an energy value of a monochromatic image by comparing a representative value of physical quantities of the object on the basis of regions of the object with pre-stored reference values.

Specifically, referring to FIG. 8, the image processor 126 arranges the physical quantities of the object on the basis of regions in order of magnitude of the physical quantities to determine the representative value of the physical quantities of the object on the basis of regions of the object in the Z-axis direction. The physical quantities arranged in order of magnitude of the physical quantities may have values shown in a lower graph of FIG. 8.

In addition, the image processor 126 may select a physical quantity having a preset magnitude ratio as the representative value of the physical quantities of the object on the basis of regions. For example, the preset magnitude ratio may be a ratio between a given physical quantity and the maximum physical quantity of the object.

For example, when the physical quantities of the object on the basis of regions are arranged in the order of magnitude and expressed as percentiles as illustrated in FIG. 9, the image processor 126 may select a physical quantity Lx corresponding to the 90th percentile that is the preset magnitude ratio as a representative value of the physical quantity of the object.

In addition, the image processor 126 determines an energy value of the monochromatic image based on the selected representative value Lx. Hereinafter, a process of determining the energy value of the monochromatic image will be described with reference to FIGS. 10 and 11.

Figure 10:
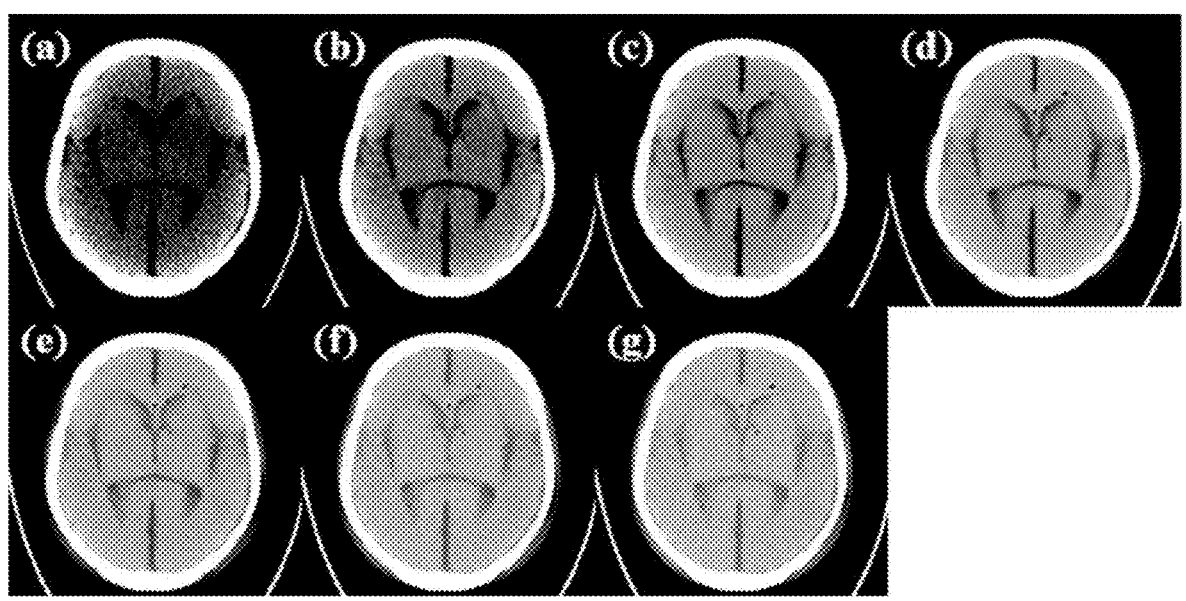
FIG. 10 illustrates a plurality of monochromatic images respectively corresponding to a plurality of energy values.
Figure 11:
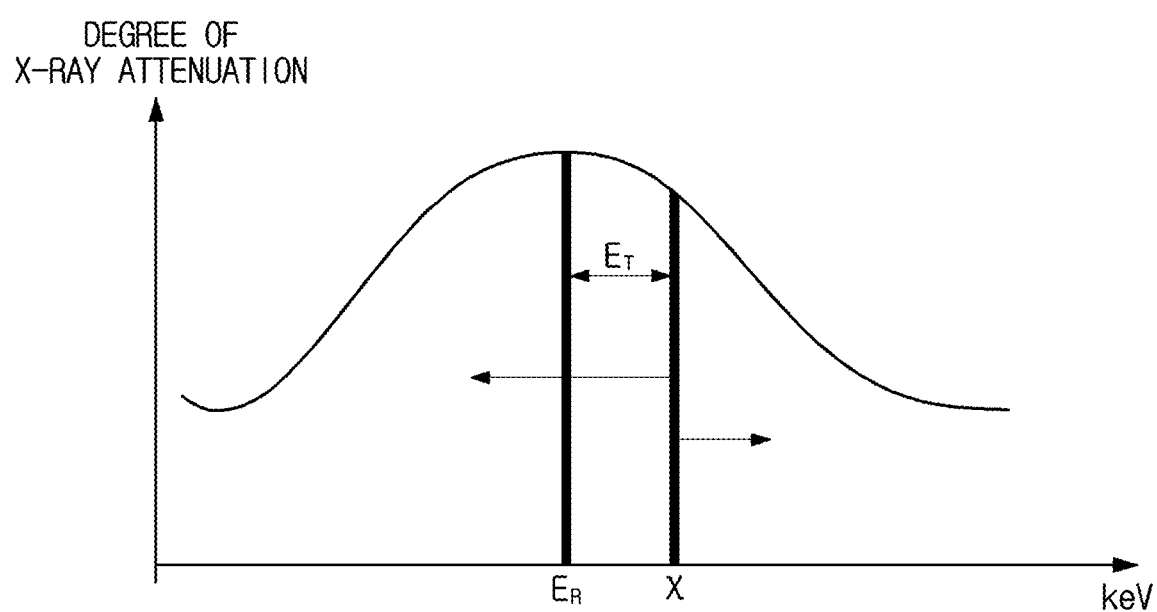
FIG. 11 is a graph illustrating degrees of X-ray attenuation of a plurality of monochromatic images with respect to a selected energy value.

FIG. 10 illustrates a plurality of monochromatic images respectively corresponding to a plurality of energy values. FIG. 11 is a graph illustrating degrees of X-ray attenuation of a plurality of monochromatic images with respect to a selected energy value.

Referring to FIG. 10, the image processor 126 may create a plurality of monochromatic images respectively corresponding to energy values (a) 40 keV, (b) 50 keV, (c) 60 keV, (d) 70 keV, (e) 80 keV, (f) 90 keV, and (g) 100 keV. Among these energy values, one energy value (e.g., (c) 60 keV) and a physical quantity corresponding to the energy value may be preset as a reference energy value and a reference physical quantity in the stage of production. The reference energy value and the reference physical quantity may also be preset by the user.

The image processor 126 compares the selected representative physical quantity Lx with the preset reference physical quantity to determine a monochromatic image suitable for a body size of the object.

Referring to FIG. 11, if the representative physical quantity Lx of the object is equal to or greater than the preset reference physical quantity, the image processor 126 increases the energy value x from the reference energy value ER. If the representative physical quantity of the object is less than the reference physical quantity, the image processor 126 decreases the energy value x from the reference energy value ER.

In this case, the image processor 126 may calculate a difference between the representative physical quantity Lx of the object and the preset reference physical quantity and determine the degree ET of the energy value x to be increased or decreased from the reference energy value ER in proportion to the difference.

In addition, the image processor 126 may generate the monochromatic image as a final cross-sectional image by extracting data of the primary cross-sectional image having the selected energy value x.

Figure 12:
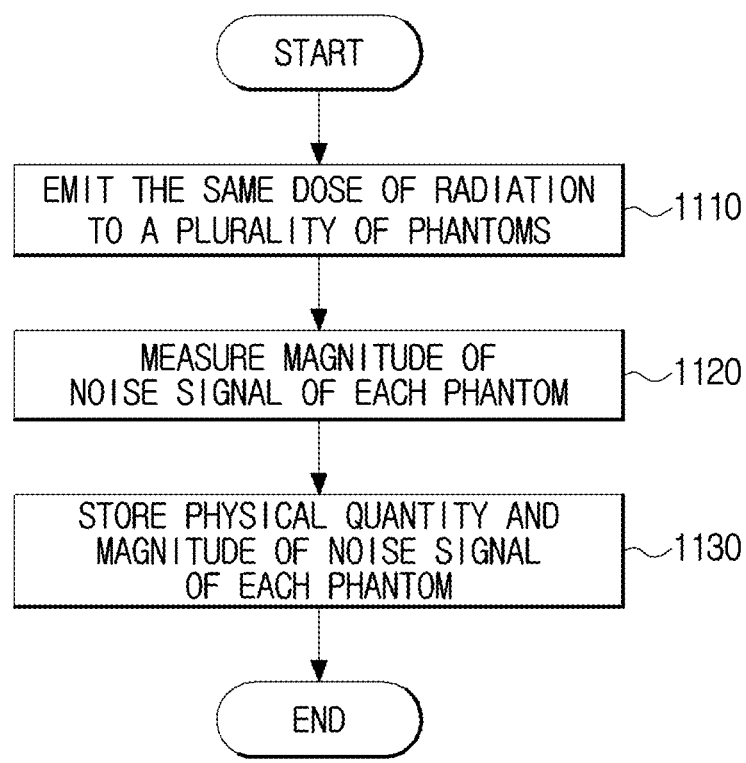
FIG. 12 is a flowchart for describing a method of creating a mapping table of the CT apparatus.
Figure 13:
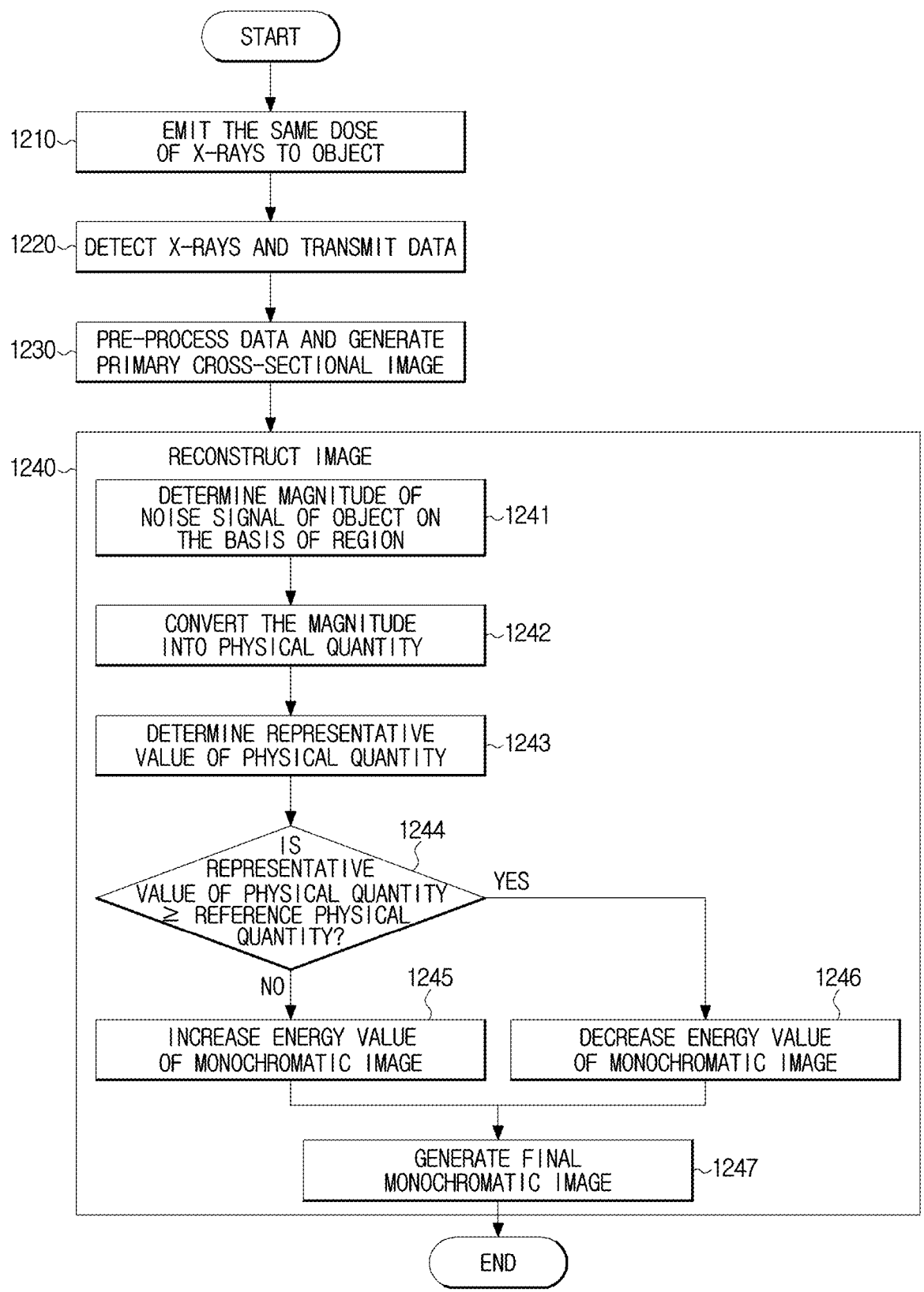
FIG. 13 is a flowchart for describing a method of controlling the CT apparatus.

Hereinafter, a method of controlling the CT apparatus 100 according to an embodiment will be described with reference to FIGS. 12 and 13. FIG. 12 is a flowchart for describing a method of creating a mapping table of the CT apparatus. FIG. 13 is a flowchart for describing a method of controlling the CT apparatus.

Since elements of the CT apparatus 100 to be described below with reference to FIGS. 12 and 13 are the same as those of the CT apparatus 100 described above with reference to FIGS. 1 to 11, the same reference numerals will be used.

First, referring to FIG. 12, the X-ray generator 106 and the collimator 112 according to an embodiment generate X-rays and emit the same dose of X-rays to a plurality of phantoms having different physical quantities to obtain a mapping table (1110).

Next, the X-ray detector 108 detects X-rays received through each of the phantoms and data on the detected X-rays is transmitted to the image processor 126 via the DAS 116 and the data transmitting unit 120. Then, the image processor 126 generates a plurality of cross-sectional images respectively corresponding to the plurality of phantoms based on the data on the received X-rays and measures magnitudes of noise signals of the respective cross-sectional images (1120).

Then, the image processor 126 stores physical quantities of the plurality of phantoms and the magnitudes of the noise signals as a mapping table (1130). The physical quantities of the phantoms may be values input by the user or acquired from tags attached to or chips embedded in the phantoms.

Hereinafter, a method of controlling the CT apparatus 100 according to an embodiment to select an optimal energy value for the object will be described with reference to FIG. 13.

First, the X-ray generator 106 and the collimator 112 generate X-rays and emit the X-rays to the object (1210). In this case, the X-ray generator 106 and the collimator 112 may generate X-rays and emit the same dose of X-rays in the Z-axis direction to generate a scout image.

Next, the X-ray detector 108 detects X-rays received through the object and data on the detected X-rays is transmitted to the image processor 126 via the DAS 116 and the data transmitting unit 120 (1220). Then, the image processor 126 pre-processes the data on X-rays received via the data transmitting unit 120 and generates a plurality of primary cross-sectional images based on the pre-processed data (1230). Accordingly, the plurality of primary cross-sectional images is generated in the Z-axis direction.

Then, in an image reconstruction process (1240), the image processor 126 determines the magnitudes of the noise signals of the object on the basis of regions of the object based on the plurality of primary cross-sectional images (1241).

Next, the image processor 126 determines physical quantities of the regions of the object on the basis of regions of the object respectively corresponding to the magnitudes of the noise signals on the basis of regions of the object (1242).

Since the noise signals and physical quantities of the object on the basis of regions of the object are described above with reference to FIG. 2, detailed descriptions thereof will not be repeated.

Then, the image processor 126 determines a representative value of the physical quantities of scout images on the basis of regions of the object (1243). In order to determine the representative value of the physical quantities of the object on the basis of regions of the object, the image processor 126 may arrange the physical quantities of the regions of the object in the order of magnitude and select a physical quantity having a preset magnitude ratio as the representative value of the physical quantities of the object on the basis of regions of the object.

Then, the image processor 126 determines an energy value of a monochromatic image based on the selected representative value (1244 to 1246).

Specifically, the image processor 126 compares the selected representative value with a preset reference physical quantity (1244). When the representative value of the object is equal to or greater than the preset reference physical quantity ("Yes" of 1244), the image processor 126 increases the energy value from the preset reference energy value (1245). When the representative value of the object is less than the preset reference physical quantity ("No" of 1244), the image processor 126 decreases the energy value from the reference energy value (1246).

In this case, the image processor 126 may calculate a difference between the representative value of the object and the preset reference physical quantity and determine the degree of the energy value to be increased or decreased from the reference energy value in proportion to the difference.

Then, the image processor 126 may generate a final monochromatic image based on the determined energy value (1247).

The generated final monochromatic image may be displayed to the user via the display unit 130 or transmitted to the server 134 via the communication unit 132.

Meanwhile, although the image processor 126 performs some of the control operations (1241 to 1246) according to the present embodiment, one of these operations may also be performed by the controller 118.

The aforementioned embodiments may be embodied in the form of a recording medium storing instructions executable by a computer. The instructions may be stored in the form of program codes and perform the operation of the disclosed embodiments by creating a program module when executed by a processor. The recording medium may be embodied as a computer readable recording medium.

The computer readable recording medium includes all types of recording media that store instructions readable by a computer such as read only memory (ROM), random access memory (RAM), magnetic tape, magnetic disc, flash memory, and optical data storage device.

As is apparent from the above description, according to the present disclosure, the energy value required to generate the monochromatic image is selected based on the body size of the patient, and thus the monochromatic image suitable for the patient may be provided.

In addition, the monochromatic image corresponding to the optimal energy value may be automatically generated even when the user does not select the energy value.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A medical imaging apparatus comprising:
an image processor configured to generate an image based on data acquired by an X-ray detector; and
a display configured to display the image,
wherein the image processor is further configured to determine a magnitude of a noise signal of a scout image of an object, determine a physical quantity of the object corresponding to the determined magnitude of the noise signal, determine an energy value of a monochromatic image by comparing the determined physical quantity of the object and a preset reference physical quantity, and generate the monochromatic image corresponding to the determined energy value, and
wherein the image processor is further configured to increase the energy value in response to the selected physical quantity of the object being equal to or greater than the preset reference physical quantity and decrease the energy value in response to the selected physical quantity of the object being less than the preset reference physical quantity.

2. The medical imaging apparatus according to claim 1, wherein the image processor is further configured to determine magnitudes of noise signals of a plurality of cross-sectional images of the object, the plurality of cross-sectional images of the object corresponding to regions of the object, determine physical quantities of the object corresponding to the magnitudes of the noise signals of the plurality of cross-sectional images of the object corresponding to regions of the object, and determine the energy value of the monochromatic image by comparing a representative value of the determined physical quantities of the object with the preset reference physical quantity.

3. The medical imaging apparatus according to claim 2, wherein the image processor is further configured to select a physical quantity having a preset magnitude ratio as the representative value of the determined physical quantities of the object.

4. The medical imaging apparatus according to claim 1, wherein the image processor is further configured to increase or decrease the energy value in proportion to a difference value between the selected physical quantity of the object and the preset reference physical quantity.

5. The medical imaging apparatus according to claim 1, further comprising an input unit configured to input the energy value,
wherein the image processor is further configured to generate the monochromatic image corresponding to the energy value input via the input unit.

6. The medical imaging apparatus according to claim 5, wherein the input unit is further configured to receive an instruction to enter an automatic mode or a manual mode, and
the image processor is further configured to generate the monochromatic image corresponding to the determined energy value in response to the input unit receiving the instruction to enter the automatic mode and generate the monochromatic image corresponding to the input energy value in response to the input unit receiving the instruction to enter the manual mode.

7. The medical imaging apparatus according to claim 2, wherein the physical quantities of the object comprise a diameter of a cross-section of the object or a volume of the object shown in the scout image.

8. The medical imaging apparatus according to claim 1, further comprising:
a gantry comprising:
an X-ray generator configured to emit X-rays; and
the X-ray detector configured to detect X-rays generated by the X-ray generator and received through the object; and
a table on which the object is positioned, the table being configured to move into and out of the gantry.

9. The medical imaging apparatus according to claim 2, further comprising:
a gantry comprising:
an X-ray generator configured to emit X-rays; and
the X-ray detector configured to detect X-rays generated by the X-ray generator and received through the object; and
a table on which the object is positioned, the table being configured to move into and out of the gantry,
wherein the image processor is further configured to generate a plurality of scout images in one direction of the object based on data acquired by the X-ray detector, and
wherein the image processor is further configured to determine magnitudes of noise signals of the plurality of scout images as the magnitudes of the noise signals of the plurality of cross-sectional images of the object.

10. The medical imaging apparatus according to claim 9, wherein the one direction is a direction in which the table is configured to move into and out of the gantry.

11. The medical imaging apparatus according to claim 1, wherein the medical imaging apparatus comprises a computed tomography imaging apparatus.

12. A method of controlling a medical imaging apparatus, the method comprising:
generating a scout image of an object based on data acquired by an X-ray detector;
determining a magnitude of a noise signal of the scout image;
determining a physical quantity of the object corresponding to the determined magnitude of the noise signal;
determining an energy value of a monochromatic image by comparing the determined physical quantity of the object with a preset reference physical quantity; and
generating the monochromatic image corresponding to the determined energy value,
wherein the determining of the energy value of the monochromatic image is performed by increasing the energy value when the selected physical quantity of the object is equal to or greater than the preset reference physical quantity and decreasing the energy value when the selected physical quantity of the object is less than the preset reference physical quantity.

13. The method according to claim 12, wherein the determining of the magnitude of the noise signal is performed by determining magnitudes of noise signals of a plurality of cross-sectional images of the object, the plurality of cross-sectional images of the object corresponding to regions of the object,
the determining of the physical quantity of the object is performed by determining physical quantities of the object corresponding to the magnitudes of the noise signals of the plurality of cross-sectional images of the object, and
the determining of the energy value of the monochromatic image is performed by comparing a representative value of the determined physical quantities of the object with the preset reference physical quantity.

14. The method according to claim 13, wherein the determining of the energy value of the monochromatic image comprises selecting a physical quantity from among the determined physical quantities having a preset magnitude ratio as the representative value of the physical quantities of the object.

15. The method according to claim 12, wherein the determining of the energy value of the monochromatic image comprises increasing or decreasing the energy value in proportion to a difference between the selected physical quantity of the object and the preset reference physical quantity.

16. The method according to claim 12, wherein the generating of the scout image of the object is performed by generating a plurality of scout images in one direction of the object, and
the determining of the magnitude of the noise signal of the scout image is performed by determining magnitudes of noise signals of the plurality of scout images.

17. The method according to claim 16, wherein the medical imaging apparatus includes a gantry configured to emit and detect X-rays and a table on which the object is positioned and configured to move into and out of the gantry, and
wherein the one direction is a direction in which the table is configured to move into and out of the gantry.

18. The method according to claim 12, further comprising storing a mapping table comprising physical quantities mapped to magnitudes of noise signals based on cross-sectional images of a phantom, the cross-sectional images of the phantom being obtained before receiving data,
wherein the determining of the physical quantity of the object is performed by determining physical quantities of the object corresponding to the determined magnitudes of the noise signals based on the mapping table.

* * * * *